United States Patent
Heinonen

(10) Patent No.: US 7,681,574 B2
(45) Date of Patent: *Mar. 23, 2010

(54) METHOD AND APPARATUS FOR DETERMINING FUNCTIONAL RESIDUAL CAPACITY OF THE LUNGS

(75) Inventor: Erkki Heinonen, Helsinki (FI)

(73) Assignee: General Electric Company, Helsinki (FI)

( * ) Notice: Subject to any disclaimer, the term of this patent is extended or adjusted under 35 U.S.C. 154(b) by 666 days.

This patent is subject to a terminal disclaimer.

(21) Appl. No.: 11/315,929

(22) Filed: Dec. 22, 2005

(65) Prior Publication Data

US 2007/0144520 A1    Jun. 28, 2007

(51) Int. Cl.
*A61M 16/00* (2006.01)
*A62B 7/00* (2006.01)
*F16K 31/02* (2006.01)

(52) U.S. Cl. ............... 128/204.21; 128/204.18; 128/204.22; 600/538; 600/529

(58) Field of Classification Search ........... 128/200.24, 128/204.22, 204.26, 204.29, 204.18, 204.21, 128/203.12, 203.25; 600/538, 529, 532
See application file for complete search history.

(56) References Cited

U.S. PATENT DOCUMENTS

| | | | | |
|---|---|---|---|---|
| 4,307,730 A * | 12/1981 | Korn | ...................... | 600/541 |
| 4,418,701 A * | 12/1983 | Luijpers | ...................... | 600/542 |
| 5,540,233 A * | 7/1996 | Larsson et al. | ............... | 600/538 |
| 5,584,300 A * | 12/1996 | Gaides | ...................... | 600/538 |
| 5,957,128 A * | 9/1999 | Hecker et al. | .......... | 128/204.22 |
| 6,139,506 A * | 10/2000 | Heinonen | ...................... | 600/532 |
| 6,306,099 B1 * | 10/2001 | Morris | ...................... | 600/529 |
| 6,544,191 B2 * | 4/2003 | Koch et al. | ................. | 600/538 |
| 2002/0052560 A1 | 5/2002 | Koch et al. | | |
| 2004/0249301 A1 * | 12/2004 | Stenqvist | ................... | 600/538 |

* cited by examiner

*Primary Examiner*—Danton DeMille
*Assistant Examiner*—Rachel T Young
(74) *Attorney, Agent, or Firm*—Andrus, Sceales, Starke & Sawall, LLP

(57) ABSTRACT

The functional residual capacity (FRC) value of a subject's lungs determined for each breath is related a volume dilution factor $k_n$ and the final FRC value is determined at the point where the volume dilution factor $k_n$ reaches a predetermined volume dilution factor value. The determination of the final FRC value can be based on interpolation or extrapolation from a measured breath data series. The volume dilution factor may be normalized value. This is achieved by division of all volume dilution factors with the initially determined volume dilution factor. With normalization, the compartments in which gas concentration change is achieved slowly are referenced with the faster, more effective compartments, thus giving a ventilation profile of the lungs.

18 Claims, 3 Drawing Sheets

METHOD AND APPARATUS FOR DETERMINING FUNCTIONAL RESIDUAL CAPACITY OF THE LUNGS

FIELD OF THE INVENTION

The present invention relates to a method and apparatus for determining the functional residual capacity of a subject's lungs.

BACKGROUND OF THE INVENTION

Lung volume measurement is useful in long-term intensive care to optimize lung therapy and ventilation for the pulmonary characteristics of a patient. In carrying out such therapies, the patient is often sedated, lying for long periods in an unchanged posture, and sometimes ventilated with a high oxygen concentration gas mixture. Under such conditions, the lungs tend to collapse and smaller airways gradually close at the end of expiration. Infiltrates from pulmonary perfusion may exacerbate these conditions. This gradual collapse and closure is called alveolar de-recruitment. If allowed to progress far enough, this will cause insufficient gas exchange in the lungs that may be observed, e.g. by arterial oxygen monitoring. Such de-recruitment can be reversed by periodic recruitment in which the lung is opened by providing elevated pressure breathing gases to the lungs.

However, long before the deterioration of gas exchange in the lungs becomes apparent, de-recruitment may gradually damage the lung during long-term ventilation. The mechanism behind this damage is a shearing of alveolar tissue against itself caused by cyclic opening and closing during tidal breathing. Much intensive care equipment currently lacks accessible bedside methods to observe such de-recruitment and loss of lung volume occurring in the lungs.

Methods to obtain a lung volume measurement at the bedside typically use an inert gas wash out technique. In this technique, a gas that is metabolically inert with respect to gas exchange in the lungs is provided in the inhaled breathing gases. The most common inert gases used for this purpose are sulphur hexafluoride ($SF_6$) and nitrogen ($N_2$), the latter providing advantage of already having existing concentration control in ventilator equipments since nitrogen is a component of atmospheric air. It is also possible to use an inert gas wash in technique to measure FRC.

In a state of equilibrium, the amount of inhaled inert gas equals with the amount of exhaled inert gas. To commence a lung volume measurement, the inert gas concentration in inhaled breathing gases is changed. The concentration of inert gas in the lungs is driven toward a new equilibrium. In the process of attaining the new equilibrium, a net amount of inert gas is exchanged in the lungs through breathing. Measuring the amount of this exchange and relating that with the respective change in lung inert gas concentration gives an indication of end-expiratory lung volume, namely the functional residual capacity (FRC) of the lungs. The functional residual capacity of the lungs is the volume of the lungs remaining after a normal exhalation. The FRC volume of the lungs is presented in Equation 1 as $$FRC_n = \left| \frac{\sum_{breaths=1}^{n} \Delta V^{N2}}{ETN_2^{baseline} - ETN_2^n} \right| \quad (1)$$

In Equation 1, the numerator is the volume of exhaled inert gas, such as nitrogen ($N_2$), and the denominator is the difference or change in expired end tidal nitrogen concentrations occurring during the measurement commencing from a baseline amount.

Using Equation 1, a new FRC value is determined for each breath subsequent to the change in inspired inert gas concentration. These values are not constant but tend to increase with successive breaths as the measurement moves to a termination. Criteria for concluding the measurement to establish an FRC value are therefore necessary in order to achieve the reproducibility of the FRC measurement for comparative and other purposes. Algorithms have been presented for this purpose. See, for example, U.S. Published Patent Application No. 2002/0052560 that describes a method to stop the measurement when FRC convergence to an end value appears to develop. Such convergence is defined as occurring when the FRC for a preset number of successive breaths is within a preset tolerance range. As an example, the number of breaths is presented as three and the tolerance as 5%-20% of the last calculated FRC value, with the last calculated value representing the final result for the FRC. As alternative concluding criteria, the measurement resolution of the gas concentration analyzer used in the measurement of FRC is presented. Both of these methods however lack a physiological connection with the primary function of the lung, the provision of oxygen to the blood and the removal of carbon dioxide from the blood.

SUMMARY OF THE INVENTION

The present invention relates to the measurement of lung volume and, more particularly, to a technique to improve the reproducibility of such measurements.

When performing an inert gas wash out or wash in measurement for FRC, the change in inert gas volume/breath is largest immediately after the change in inspired inert gas concentration and reduces toward the end of a succession of breaths. Theoretically, assuming a one-compartment model of the lung and perfect mixing of the breathing gases after each inspiration, the changes both in inert gas volume and concentration follow the exponential rule. However, an actual lung is not homogeneous and gas mixing is not perfect either. Therefore the rates of change are not exponential but are typically composed of a multitude of exponentials. Also, these exponentials often differ with respect to a change in inert gas volume and a change in concentration, with the concentration being that which more closely follows the one-compartment ideal model. As a result, lung volume measured with the inert gas method is not constant but increases over a series of breaths as the inert gas reaches a new equilibrium. The reference to a compartment or compartments in the lungs is to an analytical concept and does not directly refer portions of the lung anatomy, such as lobes.

Therefore, the measured volume will depend on how long the measurement continues. As noted above, to get reproducible and comparative FRC measurement results, measurement stop criteria have to be established.

The lower the ventilation, i.e. relative change of gas, in a lung compartment per breath, the more breaths that are required to reach a new equilibrium in the concentration of inert gas, after the initial change in inspired gas concentration. Moving to the new concentration equilibrium induces the change in inert gas volume. Also, the lower the ventilation in a compartment, the less significant will be the contribution of that compartment to gas exchange with blood, and the less useful these regions will be with respect to the primary function of the respiration, to deliver oxygen to the blood and remove carbon dioxide from the blood. Therefore, ventilation provides a physiological entity to which the lung volume measurement can be related.

The ventilation of a lung compartment in series of breaths can be derived from single breath gas dilution of the compartment. For an ideal one-compartment model of the lung, the new concentration $F_1$ of inert gas in a lung volume V, initially at an inert gas concentration $F_o$, after induction of an inspired and expired volume $V_A$ having an altered inert gas concentration $F_i$ can be determined from Equation 2

$$F_1 = \frac{V_A}{V + V_A} * Fi + \frac{V}{V + V_A} * F_0 \quad (2)$$

The induced volume $V_A$ may be the volume of a breath, i.e. the tidal volume $V_T$, or alternatively alveolar breath volume calculated from the breath volume by subtracting patient respiratory tract and instrumentation volumes not participating the gas exchange. For breath n in a series of breaths, the difference between the inert gas concentration in a compartment of the lung and the altered inspired gas concentration, $F_n-F_i$, relative to the concentration difference between the starting equilibrium concentration and the altered inspired inert gas concentration, $F_0-F_i$, at breath n will be $$\frac{F_n - Fi}{F_o - Fi} = k_n = \left(\frac{V}{V + V_{An}}\right)^n \quad (3)$$

where $k_n$ is a volume dilution factor after breath "n".

Whereas for the ideal one-compartment lung the volume dilution factor can be calculated from the gas concentrations, this is not true for real multi-compartment lungs. Calculated from the concentrations, the best ventilated compartment dominates in contribution to the $F_n$ approaching the value of $F_i$ too fast and the slow compartments would become unobserved. However, even in these circumstances the derivation for a one-compartment lung can be useful by using the volumes to calculate the volume dilution factor $k_n$ for the breath n. For this purpose, equation (3) can be rewritten as $$k_n = k_{n-1} \cdot \left(\frac{V_n}{V_n + V_{An}}\right) \quad (4)$$

where $k_{n-1}$ is the volume dilution factor for the previous breath and $V_n$ is the lung volume measured at breath n. From equation 3 we get $k_o=1$.

According to the invention, the FRC value determined for each breath is related to the volume dilution factor $k_n$ and the final FRC value is determined at the point where the volume dilution factor $k_n$ reaches a predetermined dilution factor value. The determination of the final FRC value can be based on interpolation or extrapolation from the measured breath data series. In a preferred embodiment of the invention, interpolation is favored for better accuracy. For this purpose, the measurement is continued one or more breaths beyond the breath where the dilution factor goes beyond the predetermined fixed dilution factor.

In another aspect of the invention, the volume dilution factor may be normalized value. This is achieved by division of all volume dilution factors with the initially determined volume dilution factor. With normalization, the compartments in which gas concentration change is achieved slowly are referenced with the faster, more effective compartments, thus giving a ventilation profile of the lung.

DETAILED DESCRIPTION

Figure 1:
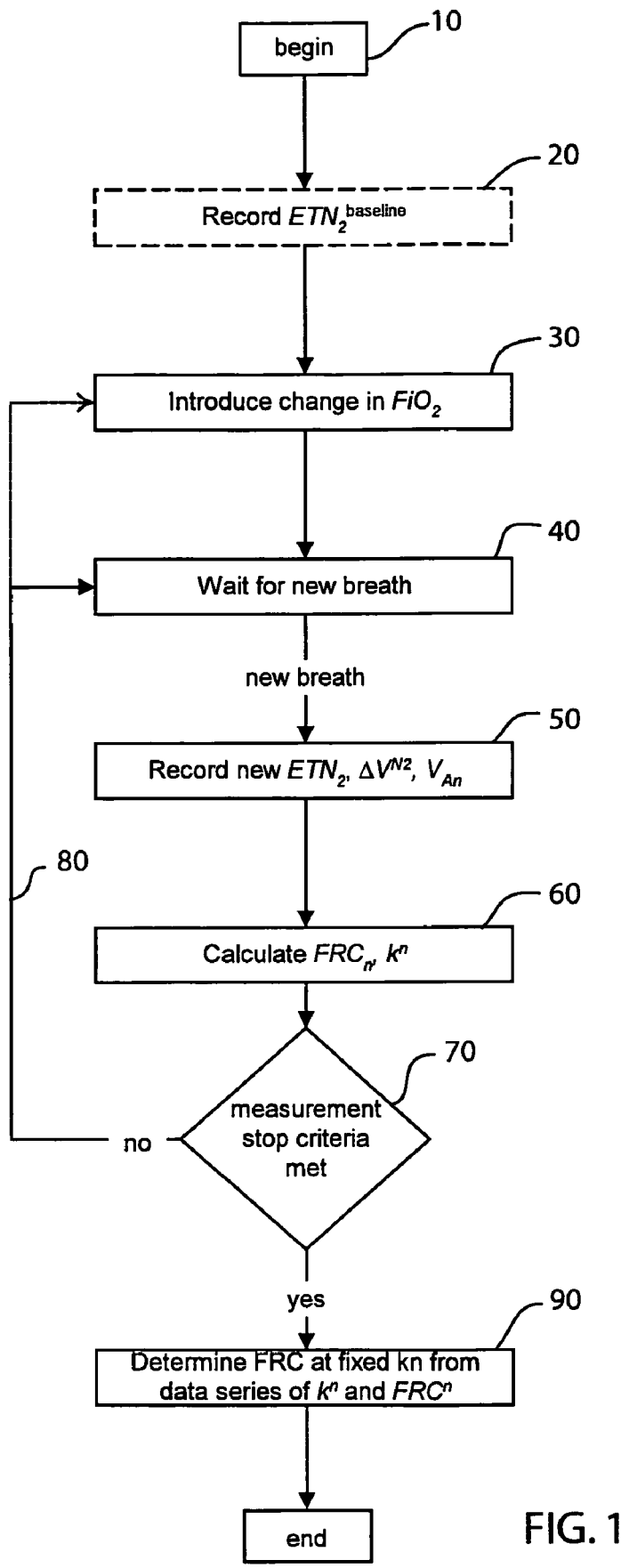
FIG. 1 presents a flow diagram of the FRC measurement process of the present invention.

FIG. 1 shown FRC measurement process of the present invention. Following the beginning of the measurement process at step 10, the existing or baseline concentration of an inert tracer gas in the lungs of the subject is ascertained. This is done at step 20 by determining the end-tidal (ET) concentration of the tracer gas. For exemplary purposes, nitrogen ($N_2$), used as the tracer gas so the measured concentration is $ETN_2$. This step may, however, be omitted if the baseline concentration is otherwise known or obvious. This could be the situation where the initial concentration is e.g. zero.

After the determination of step 20, the measurement of FRC can be started by initiating a change in the inspired gas concentration of nitrogen at step 30. In FIG. 1, this is shown as being carried out by altering the concentration of inspired oxygen $FiO_2$ since this can be easily accomplished when the subject is breathing with the aid of a ventilator. For a given induced $V_A$, increasing the concentration of $O_2$ will decrease the concentration of $N_2$. This change preferably occurs rapidly, for example within one breath, or within the initial breaths of a series of breaths. However, the method is not limited to this but can be utilized with other forms of inspired gas concentration change patterns as well.

Step 40 represents a pause awaiting a breath following the change in inspired tracer gas concentration in step 30. A breath is defined here as a sequence comprising an inspiration followed by a expiration. Preferably for the accuracy of the FRC measurement, all the breaths after the initial change in inspired tracer gas concentration are recorded. When the new breath occurs, it is analyzed for the change in tracer gas volume $\Delta V^{N2}$, ventilation volume $V_{An}$ as well as tracer gas concentration $ETN_2$ in the subject's lungs. This occurs in step 50.

Using the foregoing data, a FRC value and a dilution factor $k_n$ are calculated at step 60 for the breath using Equations 1 and 4 respectively and the values are entered into a sequential array of breath data for use in the final analysis of FRC. If relative or normalized dilution factors are to be used, the first value for $k_n=k_1$ is recorded as a denominator to which subsequent dilution factors are related to as numerators. This will scale the dilution factor $k_n$ with the best-ventilated portion of the lung, producing a ventilation profile of the lung rather than just an absolute indication of lung ventilation. This results in better comparability between successive measurements. Step 60, as described, is not necessary in order to carry out the method of the present invention but is convenient for the user in providing a real-time view of lung properties as the measurement proceeds. That is, the FRC calculations of step 60 can be performed once for all breaths after the stop criteria for the dilution factor have been fulfilled at step 70 or can be performed as the breaths occur using step 60. While use of Equation 4 is closely related to the physiological processes occurring in the lung, the invention is not limited to the use of Equation 4 for determining the dilution factor, but can use some other determination of volume dilution factor $k_n$, based on lung ventilation and volume.

The criteria for stopping the FRC measurement employs the dilution factor $k_n$, either alone or with other, related criteria such as stability of the lung gas concentration, time, number of breaths, and ventilation volume after the change in inspired concentration. Preferably the measurement of FRC continues at least until a predetermined dilution factor k value is achieved, as determined in step 70. Further, and preferably, it is continued after the predetermined dilution factor value has been reached. This eliminates the need for extrapolating the final FRC value beyond determined data points. It will be appreciated that interpolation is more accurate than extrapolation, since there will be data points on both sides of the point of interest, i.e. the final FRC value.

If the stop criteria are not met after a breath, the process returns to wait for the next breath at step 40 as shown at 80 in FIG. 1. This return may also route through step 30 (dashed line) if the inspired tracer gas concentration is changed in more complex pattern than a single step change.

If the stop criteria are met in step 70, a final FRC value is determined at step 90 from the sequential sets of dilution factors and FRC values determined for the breaths and calculated at step 60. This determination may be based on linear regression analysis of the data, or other least-square-fit analysis method, resolving first the best-fit curve coefficients and then determining the final value using these coefficients. This method can be used both for interpolation or extrapolation. Alternatively, the breath for which the dilution factor is closest to the fixed value may be adopted directly as the final FRC value, but in this case the result is subject to the greater amount of inaccuracy involved in the use of a single point value.

Figure 2:
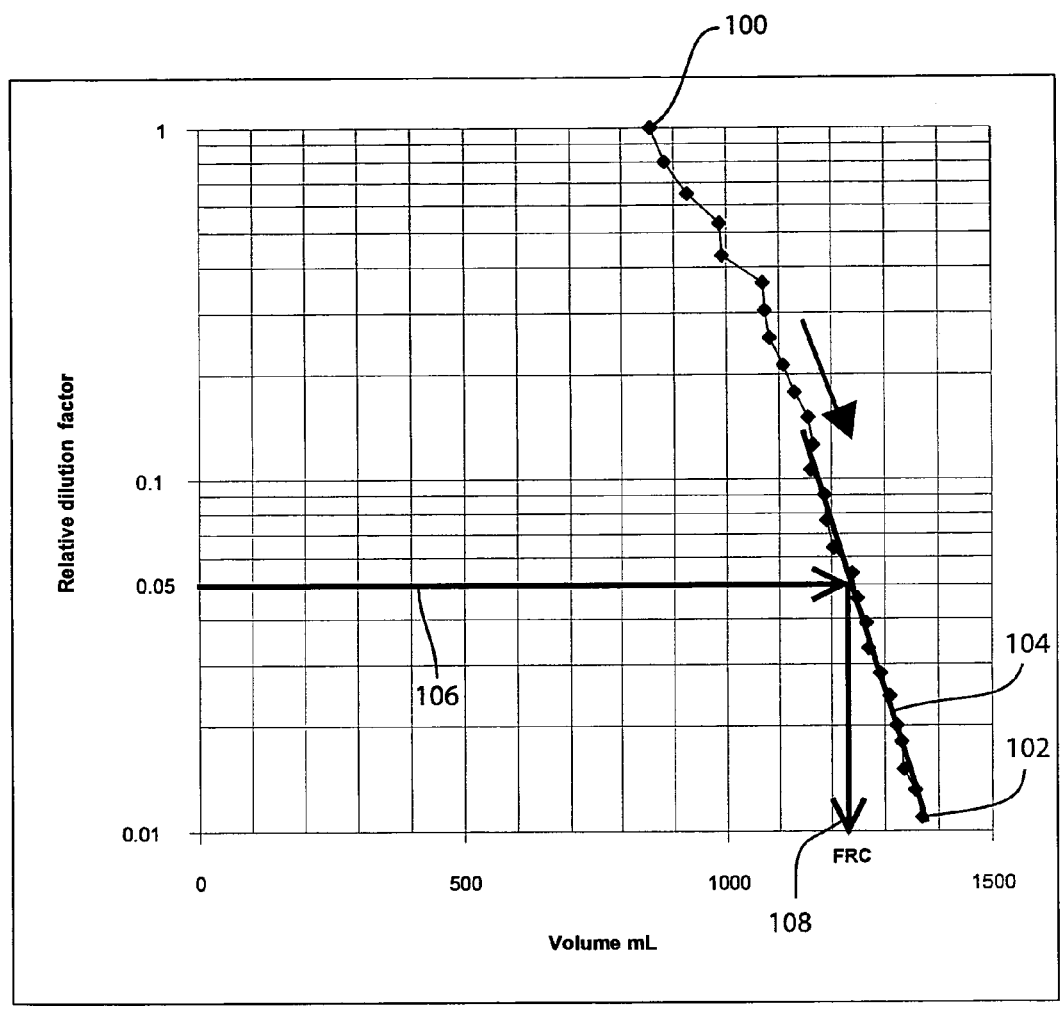
FIG. 2 presents the result of an FRC measurement in accordance with the present invention and in which dilution factor values have been normalized.

FIG. 2 graphically shows a measurement of FRC using the method of the present invention and relates FRC on the abscissa to the dilution factor $k_n$ on the ordinate. The dilution factor $k_n$ shown in FIG. 2 is a relative factor that has been normalized to the initially determined dilution factor in the manner described above. The graph begins from the first breath 100 after a step change in inspired tracer gas concentration and ends up in sequence to the last point 102 beyond which the measurement stop criteria are met. For breath 100, and for each breath thereafter, FRCn and $k_n$ is calculated as at step 60 and the quantities used to make a plot in FIG. 2. For FRC, the calculated value will tend to increase with each breath but at decreasing rates of change as the fast, well ventilated lung compartments reach equilibrium and thereafter FRC increases come from the slower less efficient lung compartments. For the dilution factor $k_n$, it will decrease for each breath as the $k_{n-1}$ is multiplied with a factor smaller than one in Equation 4. FIG. 2 shows the resulting series of plots, using a logarithmic ordinate scale, in a downwardly sloping direction.

The fixed, predetermined relative dilution factor used in the example of FIG. 2 to terminate the FRC measurement is 0.05. This means that volumes having ventilation greater than 5% of the best-ventilated areas are included in the FRC determination. The best exponential fit line 104 is calculated for data points at either side of the fixed dilution factor value, i.e. excluding the first breaths representing data from the fastest lung compartments. The first breaths are preferably excluded since they obey different exponentials than the later and concluding breaths as shown by the nature of the plots and best fit line 104 in FIG. 2. In the example of FIG. 2, the final FRC value is that the value along line 104 for a relative dilution factor 0.05 indicated by line 106 and is read from the abscissa at 108 giving an FRC value of about 1230 mL.

FIG. 2 shows obtaining the final FRC value by interpolation along line 104. It will be appreciated from linear relationship of sequential data sets that line 104 could be established by the data sets immediately following a dilution factor value of 0.1, or some other value, and point 108 determined by extrapolation along the line so established.

Figure 3:
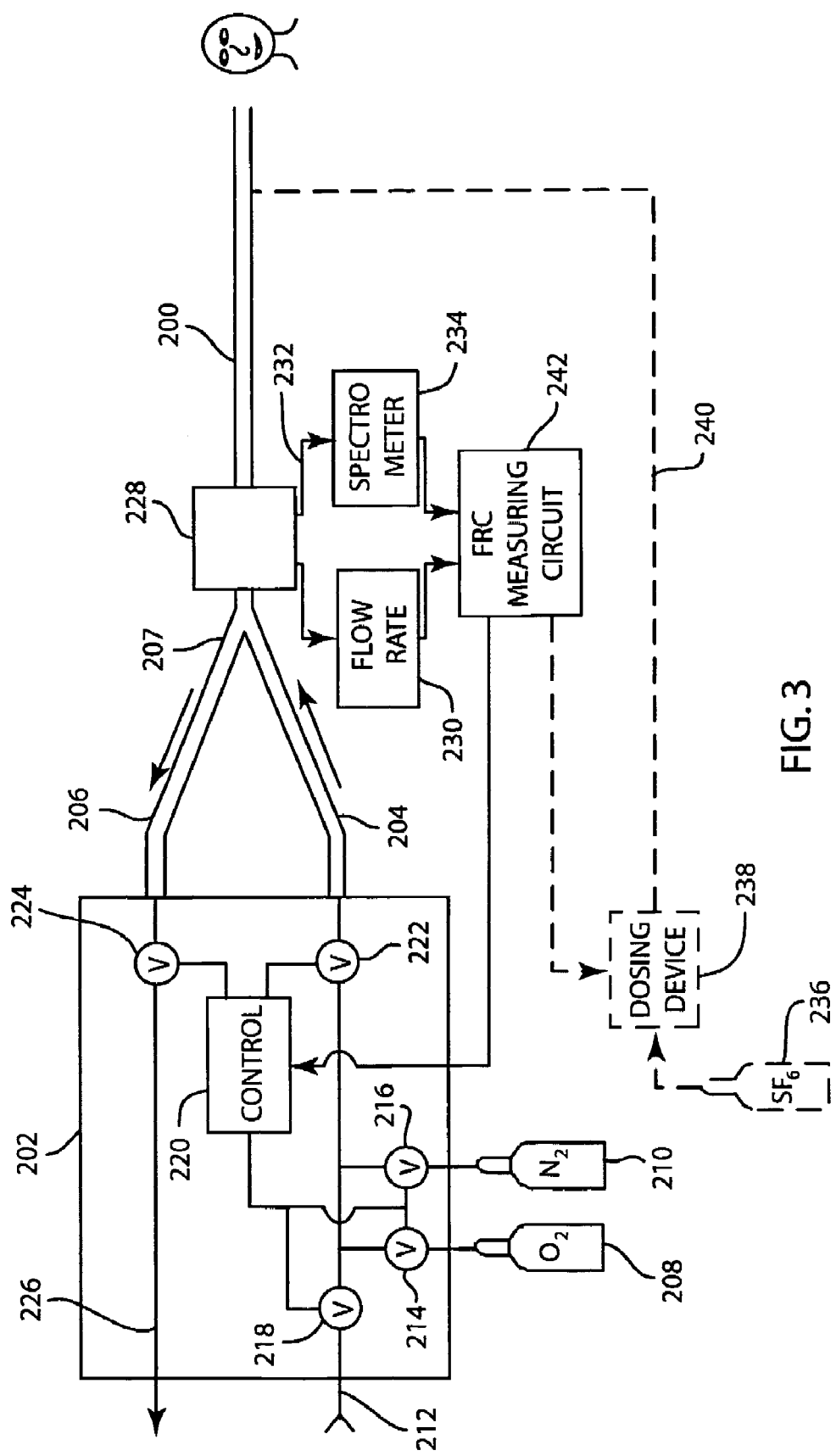
FIG. 3 is a schematic diagram of apparatus of the present invention.

FIG. 3 shows apparatus in accordance with the present invention. The subject breathes breathing gases through a breathing circuit including breathing tube 200. Tube 200 may be connected to a face mask for the subject or tube 200 may be an endotracheal tube placed in the trachea of the subject. The subject may breath spontaneously or with the assistance of a ventilator or other breathing apparatus 202 through breathing circuit components comprising an inhalation limb 204 and an exhalation limb 206 connected through Y connector 207 to breathing tube 200.

If a ventilator is being used, the breathing gases for the subject may be provided from gas supplies such as pressurized gas cylinders 208 and 210, as well as through conduit 212 providing ambient air. Valves 214, 216, and 218, controlled by control 220 determine the composition of gases inhaled by the subject.

Control 220 also determines the rate of breathing, the amount of inhalation gases provided to the patient, the amount of end pressure to which the patient is subjected, and other aspects of the subject's breathing by means of inhalation valve 222 and exhalation valve 224. Inhalation valve 222 is connected to inhalation limb 204. Exhalation valve 224 is connected to exhalation limb 206 and typically discharges the exhaled gases to the atmosphere, as through conduit 226.

A flow sensor 228 is provided in breathing tube 200 or the ventilator for determining the gas flow rate in the breathing tube, particularly during the exhalation phase of the respiratory cycle. Flow sensor 228 may be of any suitable type, for example, a pneumotachograph that utilizes the pressure drop across a flow restrictor, a turbine wheel, or an anemometer, for determining the flow. The output of flow sensor 228 is provided to circuitry 230 for converting the physical phenomenon occurring in the flow sensor to a signal indicative of the gas flow rate. Flow sensor 228 or breathing tube 200 may also include a connection for sampling conduit 232 connected to a device 234 for determining tracer gas concentration or other selected components of the breathing gases in breathing conduit 200. Such a concentration determining device may comprise an infrared spectrometer, a mass spectrometer, or other suitable means. Alternatively, a gas concentration sensor may be interposed directly in the breathing circuit to measure gas concentrations in the breathing circuit.

The tracer gas may also be provided from a pressurized tank source 236 separate from the ventilator. This could be the case when a gas such as helium, argon or sulphur hexafluorine ($SF_6$) is used as the tracer gas. A dosing device, such as an electrically controlled valve 238 is connected to the outlet of tracer gas source 236. Dosing device 238 provides controlled amounts of tracer gas to supply line 240 for provision to breathing tube 200. Dosing device 238 is controlled by functional residual capacity measuring circuit 242. Functional residual capacity measuring circuit 242 also receives inputs from flow rate circuit 230 and concentration determining device 234.

Functional residual capacity measuring circuit 242 carries out the steps shown in FIG. 2 to determine the functional residual capacity of the subject. The gas flow rates determined by flow sensor 228 and circuit 230 may be integrated with respect to time to obtain gas volumes. Concentration determining device 234 determines the end tidal nitrogen concentrations. $ETN_2$ and, taken in conjunction with the obtained gas volumes, determines tracer gas volumes.

Functional residual capacity measuring circuit 242 contains a suitable centered processing unit for determining the volume dilution factor $k_n$ and FRC in the manner described above. Circuit 242 also operates control 220 and/or closing device 238 to alter the concentration of tracer gas in the breathing gases for the subject.

Various alternatives and embodiments are contemplated as being within the scope of the following claims particularly pointing out and distinctly claiming the subject matter regarded as the invention.

What is claimed is:

1. A method for determining the functional residual capacity of a subject's lungs using a washout/wash-in technique in which a concentration of a tracer gas in the inspired breathing gases for the subject is altered from an initial concentration, said method comprising the steps of:
   (a) providing a functional residual capacity (FRC) measuring circuit having a central processing unit (CPU);
   (b) determining in the CPU, for each of a plurality of breaths of a series of breaths, a value of a volume dilution factor $k_n$, where the volume dilution factor is calculated using tidal volume and lung volume for each breath;
   (c) determining in the CPU, for each breath of the plurality of breaths, a value of the functional residual capacity of the subject's lungs;
   (d) establishing a predetermined value for the volume dilution factor $k_n$;
   (e) determining in the CPU when the value of the volume dilution factor $k_n$ determined in step (b) stands in a predetermined relationship to the predetermined value for the volume dilution factor $k_n$;
   (f) establishing a relationship in the CPU between the determined value for the volume dilution factor $k_n$ and the functional residual capacity of a subject's lungs over the plurality of breaths; and
   (g) estimating the functional residual capacity of the subject's lungs in the CPU at the predetermined value for the volume dilution factor $k_n$ based upon the established relationship of step (f).

2. The method according to claim 1 wherein step (b) is further defined as determining, for each breath of the series of breaths, the value of a volume dilution factor $k_n$ where $$k_n = k_{n-1} \cdot \left( \frac{V_n}{V_n + V_{An}} \right)$$

and $k_{n-1}$ is the volume dilution factor for a previous breath, $V_n$ is the lung volume measured at breath n and $V_{An}$ is the tidal volume for the measured breath n.

3. The method according to claim 1 further including the step of normalizing the value of the volume dilution factor $k_n$ determined in step (b) for each of the breaths of the series of breaths.

4. The method according to claim 3 further defined as obtaining a value of the factor $k_n$ for an initial breath of the series of breaths and as normalizing the volume dilution factor values obtained in subsequent breaths of the series to the initially obtained volume dilution factor value.

5. The method according to claim 1 further defined as using additional criteria in determining FRC.

6. A method for determining the functional residual capacity of a subject's lungs using a washout/wash-in technique in which the concentration of a tracer gas in the inspired breathing gases for the subject is altered from an initial concentration, said method comprising the steps of:
   (a) providing a functional residual capacity (FRC) measuring circuit having a central processing unit (CPU);
   (b) determining a functional residual capacity (FRC) value in the CPU for the subject's lungs for each of a plurality of breaths of a series of breaths;
   (c) determining in the CPU, for each of the plurality of breaths of the series of breaths, a value of a volume dilution factor $k_n$, where the volume dilution factor is calculated using tidal volume and lung volume for each breath;
   (d) establishing a relationship between the functional residual capacity value determined in step (b) to the volume dilution factor value $k_n$ determined in step (c) for the plurality of breaths of the series of breaths;
   (e) determining in the CPU when the value of the volume dilution factor $k_n$ determined in step (c) stands in a predetermined relationship to a predetermined value for the volume dilution factor $k_n$; and
   (f) determining an estimated functional residual capacity value in the CPU based upon the predetermined relationship established in step (e) between the functional residual capacity value determined in (b) and the volume dilution factor $k_n$ determined in (c), wherein the estimated functional residual capacity value is the functional residual capacity of the subject's lungs at the predetermined value for the volume dilution factor $k_n$.

7. The method according to claim 6 wherein step (c) is further defined as determining, for each breath of a series of breaths, the value of a volume dilution factor $k_n$ where $$k_n = k_{n-1} \cdot \left( \frac{V_n}{V_n + V_{An}} \right)$$

and $k_{n-1}$ is the volume dilution factor for a previous breath, $V_n$ is the lung volume measured at breath n and $V_{An}$ is the tidal volume for the measured breath n.

8. The method according to claim 6 further including the step of normalizing the values of the factor $k_n$ determined in step (c) for each breath of the series of breaths.

9. The method according to claim 8 further defined as obtaining a value of the factor $k_n$ for an initial breath of the series of breaths and as normalizing factor values obtained in subsequent breaths of the series to the initially obtained factor value.

10. The method according to claim 6 further defined as applying a statistical process to the functional residual capacity value—dilution factor value relationships for establishing a linear expression between the functional residual capacity values and the dilution factor values.

11. The method according to claim 10 wherein the statistical process is applied using functional residual capacity values for breaths at which the volume dilution factor k value is less than and more than the predetermined value for factor k and wherein the functional residual capacity of the subject's lungs is estimated by interpolation.

12. The method according to claim 10 wherein step (f) employs extrapolation from the functional residual capacity values and the dilution factor values determined for the breaths.

13. The method according to claim 10 further including the step of excluding data from a predetermined number of initial breaths of the series of breaths data sets.

14. The method according to claim 6 further defined as carrying out steps (b), (c), and (d) for all breaths of the series of breaths.

15. The method according to claim 6 further defined as carrying out step (b) as the breaths of the series occur.

16. The method according to claim 6 further defined as carrying out steps (b) and (d) as the breaths of the series occur.

17. The method according to claim 6 wherein step (b) is carried out when the value for volume dilution factor k stands in a predetermined relationship to the predetermined value for volume dilution factor k.

18. The method according to claim 6 wherein step (f) is further defined as using additional criteria in determining FRC.

* * * * *